United States Patent
Van Gemen et al.

(10) Patent No.: US 6,312,928 B1
(45) Date of Patent: Nov. 6, 2001

(54) TRANSCRIPTION BASED AMPLIFICATION OF DOUBLE STRANDED DNA TARGETS

(75) Inventors: Bob Van Gemen, HV Almere; Dianne Arnoldina Margaretha Van Strijp, AG Den Bosch; Adriana Fredericke Schukkink, LH Deventer, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/554,511

(22) PCT Filed: Nov. 10, 1998

(86) PCT No.: PCT/EP98/07329

§ 371 Date: May 16, 2000

§ 102(e) Date: May 16, 2000

(87) PCT Pub. No.: WO99/25868

PCT Pub. Date: May 27, 1999

(30) Foreign Application Priority Data

Nov. 17, 1997 (EP) .................................................. 97203577

(51) Int. Cl.[7] ....................................................... C12P 19/34
(52) U.S. Cl. .......................... 435/91.1; 435/91.2; 435/5; 435/6
(58) Field of Search .................................. 435/91.1, 91.2, 435/5, 6

(56) References Cited

FOREIGN PATENT DOCUMENTS

| 2102963 | 5/1994 | (CA) . | |
|---|---|---|---|
| 42 38 699 | 11/1992 | (DE) . | |
| 0 329 822 | * 8/1988 | (EP) | ......................................... 435/6 |
| WO 96 02668 | 2/1996 | (WO) . | |

OTHER PUBLICATIONS

T. Kievits et al., "NASBA Isothermal Enzymatic In Vitro Nucleic Acid amplification Optimized for the Diagnosis of HIV–1 Infection," Journal of Virological Methods, 35, 1991, pp. 273–286.

* cited by examiner

Primary Examiner—W. Gary Jones
Assistant Examiner—Janell Taylor
(74) Attorney, Agent, or Firm—Michael G. Sullivan

(57) ABSTRACT

The present invention is directed to a transcription based amplification method for the amplification of DNA targets. With the method of the present invention an isothermal transcription based amplification method is provided for the amplification of double stranded DNA. The method of the present invention for the amplification of double stranded DNA comprises the steps of contacting said double stranded DNA with at least one oligonucleotide comprising a sequence complementary to a part of the first of the two DNA strands comprised in the double stranded DNA, said oligonucleotide further comprising the sequence of a promoter recognized by a RNA polymerase; a further olignucleotide comprising a sequence complementary to a part of the second strand comprised in the double stranded DNA; an enzyme having RNA dependent DNA polymerase activity; an enzyme having DNA dependent DNA polymerase activity; an enzyme having RNase H activity; an enzyme having RNA polymerase activity, and maintaining the thus created reaction mixture under the appropriate conditions for a sufficient amount of time for the amplification to take place. The method according to the invention is particularly useful for amplifying small DNA molecules, e.g. plasmid DNA. Surprisingly, transcription based amplification can start from double stranded DNA, without the need to treat the DNA with restriction enzymes or, what is more important, to separate the strands before hand by applying heat. All reagents conventionally used with isothermal transcription based amplification reactions can simply be used on starting material containing double stranded DNA, as if it where single stranded RNA. With the present invention it has now been found that essentially the same protocols can be used for isothermal transcription based amplification of double stranded DNA. The method is particularly useful for the detection of small DNA molecules of pathogenic microorganisms enabling diagnosis. In particular the circular HIV-1 DNA molecules that are formed during the replication of the HIV-1 virus can be detected by this method. Detection of such circular HIV-1 DNA molecules indicates active replication of the virus, which can be correlated with disease progression, i.e. development of AIDS.

10 Claims, 1 Drawing Sheet

SEQUENCE LISTING

<160> NUMBER OF SEQ ID NOS: 21

<210> SEQ ID NO 1
<211> LENGTH: 54
<212> TYPE: DNA
<213> ORGANISM: HUMAN

<400> SEQUENCE: 1
aattctaata cgactcacta tagggtgcta tgtcacttcc ccttggttct ctca        54

<210> SEQ ID NO 2
<211> LENGTH: 29
<212> TYPE: DNA
<213> ORGANISM: HUMAN

<400> SEQUENCE: 2
agtgggggga catcaagcag ccatgcaaa        29

<210> SEQ ID NO 3
<211> LENGTH: 28
<212> TYPE: DNA
<213> ORGANISM: HUMAN

<400> SEQUENCE: 3
gaatgggata gagtgcatcc agtgcatg        28

<210> SEQ ID NO 4
<211> LENGTH: 50
<212> TYPE: DNA
<213> ORGANISM: HUMAN

<400> SEQUENCE: 4
aattctaata cgactcacta tagggaaaa ataaactgta aatcatattc        50

-continued

```
<210> SEQ ID NO 5
<211> LENGTH: 23
<212> TYPE: DNA
<213> ORGANISM: HUMAN

<400> SEQUENCE: 5
tttgttactg tggtagatac tac                                          23

<210> SEQ ID NO 6
<211> LENGTH: 23
<212> TYPE: DNA
<213> ORGANISM: HUMAN

<400> SEQUENCE: 6
agtacaaata tgtcattatg tgc                                          23

<210> SEQ ID NO 7
<211> LENGTH: 46
<212> TYPE: DNA
<213> ORGANISM: HUMAN

<400> SEQUENCE: 7
aattctaata cgactcacta tagggcaaga gtacatcggt caacga                 46

<210> SEQ ID NO 8
<211> LENGTH: 21
<212> TYPE: DNA
<213> ORGANISM: HUMAN

<400> SEQUENCE: 8
tcacagcggt tgctcgaagc a                                            21

<210> SEQ ID NO 9
<211> LENGTH: 25
<212> TYPE: DNA
<213> ORGANISM: HUMAN

<400> SEQUENCE: 9
cgtgcggggt tatcttaaaa gggat                                        25

<210> SEQ ID NO 10
<211> LENGTH: 42
<212> TYPE: DNA
<213> ORGANISM: HUMAN

<400> SEQUENCE: 10
aattctaata cgactcacta tagggaggga atcactgctt ga                     42

<210> SEQ ID NO 11
<211> LENGTH: 20
<212> TYPE: DNA
<213> ORGANISM: HUMAN

<400> SEQUENCE: 11
gaccgtagaa gatgaacgga                                              20

<210> SEQ ID NO 12
<211> LENGTH: 21
<212> TYPE: DNA
<213> ORGANISM: HUMAN

<400> SEQUENCE: 12
gttcaggaaa gaaaacagcc a                                            21
```

<210> SEQ ID NO 13
<211> LENGTH: 45
<212> TYPE: DNA
<213> ORGANISM: HUMAN

<400> SEQUENCE: 13
aattctaata cgactcacta tagggggatc tccacctcta ctgca    45

<210> SEQ ID NO 14
<211> LENGTH: 18
<212> TYPE: DNA
<213> ORGANISM: HUMAN

<400> SEQUENCE: 14
gaagctaaag cacttcca    18

<210> SEQ ID NO 15
<211> LENGTH: 18
<212> TYPE: DNA
<213> ORGANISM: HUMAN

<400> SEQUENCE: 15
ccatggagcg cgcgtcct    18

<210> SEQ ID NO 16
<211> LENGTH: 52
<212> TYPE: DNA
<213> ORGANISM: HUMAN

<400> SEQUENCE: 16
aattctaata cgactcacta tagggggaag gggcccggac ctcgtcagta ct    52

<210> SEQ ID NO 17
<211> LENGTH: 29
<212> TYPE: DNA
<213> ORGANISM: HUMAN

<400> SEQUENCE: 17
atcattcgca tcccgtcccg atgagcgca    29

<210> SEQ ID NO 18
<211> LENGTH: 25
<212> TYPE: DNA
<213> ORGANISM: HUMAN

<400> SEQUENCE: 18
ctgtccacct tccagcagat gtgga    25

<210> SEQ ID NO 19
<211> LENGTH: 44
<212> TYPE: DNA
<213> ORGANISM: HUMAN

<400> SEQUENCE: 19
aattctaata ctcactatag ggagatcctc aatgcggcgc ttca    44

<210> SEQ ID NO 20
<211> LENGTH: 20
<212> TYPE: DNA
<213> ORGANISM: HUMAN

<400> SEQUENCE: 20
gcttgtatga tgaccatgta    20

```
<210> SEQ ID NO 21
<211> LENGTH: 20
<212> TYPE: DNA
<213> ORGANISM: HUMAN

<400> SEQUENCE: 21
ctgctatgtc ttagaggaga                                              20
```

TRANSCRIPTION BASED AMPLIFICATION OF DOUBLE STRANDED DNA TARGETS

The present invention is directed to a transcription based amplification method for the amplification of DNA targets.

Nucleic acid amplification methods are used in the field of molecular biology and recombinant DNA technology. These methods are used to increase the number of copies of a particular nucleic acid sequence, present in small amounts and often in an environment in which a wide variety of other nucleic acid sequences, both RNA and DNA, are also present. In particular, nucleic acid amplification methods are used to facilitate the detection or quantification of nucleic acid and are important for diagnosing for example infectious disenses, inhereted dieseases and various types of cancer. Nucleic acid amplification methods have also found their applications in other fields where samples are investigated in which nucleic acid may be present in minute amounts, such as forensic sciences, archeology or to establish paternity.

Several nucleic add amplification techniques are known based on different mechanisms of action. One method for the amplification of nucleic acid is known as the "Polymerase Chain Reaction" (PCR) is described in European patent applications EP 200362 and EP 201148. PCR is a cyclic process which has double stranded DNA as target. Each cycle in the PCR process starts with the separation of a double stranded DNA target in its two complementary strands. To each strand a primer will anneal and DNA polymerases present will extend the primers along the DNA strand to which it annealed thus forming two new DNA duplexes. When the reaction mixture is heated the strands of the DNA duplexes will be separated again and a new PCR cycle can start. Thus, the PCR process produces multiple DNA copies of a DNA target. If single stranded RNA is the desired target for PCR, it has to be converted to double stranded DNA first by reverse transcriptase.

The present invention is concerned with a different class of nucleic acid amplification methods namely the transcription based amplification techniques. The techniques involve the transcription of multiple RNA copies from a template comprising a promoter recognized by an RNA polymerase. With these methods multiple RNA copies are transcribed from a DNA template that comprises a functional promoter recognized by the RNA polymerase. Said copies are used as a target again from which a new amount of the DNA template is obtained etc. Such methods have been described by Gingeras et al. in WO88/10315 and Burg et al. in WO89/1050. Isothermal transcription based amplification techniques have been described by Davey et al. in EP 323822 (relating to the NASBA method), by Gingeras et al. in EP 373960 and by Kacian et al. in EP 408295. Transcription based amplification reactions may also be performed with thermostable enzymes. Transcription based amplifications are usually carried out at a temperature around 41 degrees Celsius. These thermostable enzymes allow the reaction to be carried out at more elevated temperatures. Such a thermostable method is described in EP 682121 filed in the name of Toyo Boseki KK. The methods as described in EP 323822, EP 373960 and EP 408295 are isothermal continuous methods. With these methods four enzyme activities are required to achieve amplification: an RNA dependent DNA polymerase activity, an DNA dependent DNA polymerase activity, an RNase (H) activity and an RNA polymerase activity. Some of these activities can be combined in one enzyme, so usually only 2 or 3 enzymes are necessary. Enzymes having RNA dependent DNA polymerase activities are enzymes that synthesize DNA from an RNA template. A DNA dependent DNA polymerase thus synthesizes DNA from a DNA template. In transcription based amplification reactions a reverse transcriptase such as AMV (Avian Myoblastosis Virus) or MMLV (Moloney Murine Leukemia Virus) reverse transcriptase may be used. Such enzymes have both RNA- and DNA dependent DNA polymerase activity but also an inherent RNase activity. In addition an RNase may be added to the reaction mixture of a transcription based amplification reaction, such as E. coli RNase H.

DNA dependent RNA polymerases synthesize multiple RNA copies from a DNA template including a promoter recognized by the RNA polymerase. Examples of RNA polymerases are polymerases from E. coli and bacteriophages T7, T3 and SP6. An example of an RNA polymerase commonly used with transcription based amplification methods is T7 polymerase. Thus the promoter that is incorporated in the template used for transcribing multiple copies of RNA would then be the T7-promoter. Usually the template comprising the promoter has to be created starting from the nucleic acid comprising the target sequence. Said nucleic acid may be present in the starting material that is used as input for the amplification reaction. The nucleic acid present in the starting material will usually contain the target sequence as a part of a much longer sequence. Additional nucleic acid sequences may be present on both the 3'- and the 5'-end of the target sequence. The amplification reaction can be started by bringing together this nucleic acid from the starting material, the appropriate enzymes that together provide the above mentioned activities and at least one, but usually two, oligonucleotide(s). At least one of these oligonucleotides should comprise the sequence of the promoter.

Transcription based amplification methods are particularly useful if the input material is single stranded RNA, although single or double stranded DNA can likewise be used as input material. When a transcription based amplification method is practiced on a sample with single stranded RNA (of the "plus" sense) with additional sequences on both the 3'-end and the 5' end of the target sequence a pair of oligonucleotides that is conveniently used with the methods as described in the prior art would consist of:

a first oligonucleotide (usually referred to a "promoter-oligonucleotide") that is capable of hybridizing to the 3-end of the target sequence, which oligonucleotide has the sequence of a promoter (preferably the T7 promoter) attached to its 5 ' end (the hybridizing part of this oligonucleotide has the opposite polarity as the plus RNA used as input material).

a second oligonucleotide ("primer") which comprises the 3' end of the target sequence (this oligonucleotide has the same polarity as the plus RNA).

When such a pair of oligonucleotides, together with all enzymes having the appropriate activities, and a sufficient supply of the necessary ribonucleotides and deoxyribonucleotides are put together in one reaction mixture and are kept under the appropriate conditions (that is, under the appropriate buffer conditions and at the appropriate temperature) for a sufficient period of time an isothermal continuous amplification reaction will start. FIG. 1 gives a proposed mechanism for part of a transcription based amplification reaction known in the art. The isothermal continuous process of amplification is pictured in FIG. 1 as a cyclic process. However, in fact all steps of this process will take place at the same time since all ingredients are present in the reaction vessel. Thus, picturing the process as a particular sequence of events might be good for a better understanding of a possible mechanism underlying the amplification process, it might not be a real reflection of what is actually happening in the reaction mixture during amplification. The cycle depicted in FIG. 1 can be regarded as starting with a first amount of single stranded RNA. The RNA depicted in the cycle is RNA of the minus sense. Thus, it will be able to hybridize with the second oligonucleotide of the pair of oligonucleotides mentioned above. This minus RNA will normally not be present as such in the starting material for the amplification reaction but will be derived from, for example, the plus RNA present in the starting material through reaction with the oligonucleotides and enzymes when all ingredients of the reaction mixture have been brought together.

Many variants of the above theme have been described in the prior art. From the reaction scheme depicted in FIG. 1 it can be seen that, the second oligonucleotide (as described above) serves as a primer to prime the synthesis of a strand of DNA complementary to the minus RNA. The oligonucleotide comprising the promoter-sequence is capable of annealing to the 3' end of the extension product of the second oligonucleotide. The promoter-part of this oligonucleotide serves as a template for the elongation of the extension product of the second oligonucleotide to provide a double stranded promoter. The 3' end of the promoter-oligonucleotide may be extended by the enzyme having DNA dependent DNA polymerase activity (reverse transcriptase) but this is not necessary. To reflect the function as a template of an oligonucleotide containing a promoter sequence it is referred to as "splice-template" in some of the prior art relating to transcription based amplification (for example EP 408295 of Genprobe Inc.). The 3' end of such a "splice template" may even be blocked. In that case the capability of the "splice template" to serve as a primer is completely eliminated.

FIG. 1 gives a proposed scheme for a transcription based amplification. This scheme comprises the synthesis of single stranded RNA transcripts. As mentioned above, the starting material containing the nucleic acid to be amplified may not contain the nucleic acid in this particular form. It will not contain minus RNA of a defined length. That is why this proposed cycle of events as depicted in FIG. 1 is probably preceded by a sequence of events leading from the nucleic acid in the starting material to the first RNA transcription step. As explained above, transcription based amplification methods are particularly useful for the amplification starting from single stranded RNA. One of the oligonucleotides, the one with the promoter sequence will then presumably anneal to this single stranded RNA and will be elongated by the enzyme with RNA dependent DNA polymerase (such as reverse transcriptase). A DNA-RNA duplex is thus obtained the RNA strand of which can be digested by RNase H. The other oligonucleotide will anneal to the remaining DNA strand and will be elongated, using this strand as a template. Thus a double stranded DNA template including a functional double stranded promoter for the RNA polymerase may be created from which the first transcription step may take place. The transcripts thus obtained may enter the proposed reaction scheme as depicted in FIG. 1. In practice, this whole sequence of events, starting from the single stranded RNA in the sample, will take place as soon as all ingredients are put together, and the mixture is brought to the appropriate temperature for the enzymes to be all active. The practitioner of the method need not intervene to accomplish any of these steps.

However, when a transcription based amplification method would have to be performed on starting material comprising the target sequence only as double stranded DNA, either circular or linear, the skilled person would not expect to be able to amplify anything without first having to perform a method to get single stranded nucleic acid from the double stranded DNA present in the starting material first. He would not expect any of his oligonucleotides to be able to anneal to the DNA since it is in a double stranded confirmation. Based on the knowledge of the skilled man, regarding transcription based amplification methods, the most logic thing to do here would be to separate the strands of the double stranded DNA by applying an elevated temperature (up to a 100 degrees Celsius) to separate the DNA and let one of the oligonucleotides anneal to one of the single strands. The enzymes used with current transcription based amplification methods would not be able to withstand such a high temperature and can, in such cases, only be added after the DNA strands have been separated. When one of the oligonucleotides anneals to a single strand DNA and is elongated, double stranded DNA is created again, and the reaction mixture would have to be subjected to an elevated temperature sufficiently high to melt the double stranded DNA into its separated strands again. Again this raise in temperature will destroy the enzymes present and new enzymes will have to be added after the heat step has been applied again. The second oligonucleotide can now be added and anneal to the strand that was created from the elongated (promoter) oligonucleotide in the first step, thus creating double stranded DNA template including a double stranded functional promoter from which a first step of RNA transcription can take place. The resulting RNA transcripts may enter a cycle like depicted in FIG. 1 and the process can further be isothermal.

From the above it is evident that starting a transcription based amplification method from double stranded DNA can be a tedious process. It requires several specific actions to be taken by the practitioner; the sample has to be heated and cooled repeatedly and enzymes have to be replenished after each heating step.

Alternatively, the double stranded DNA in the starting material can be transcribed into RNA before the start of the amplification. Such an extra step can be based on an enzyme, for instance E. coli RNA polymerase, that transcribes the double stranded DNA into RNA without the presence of a promoter sequence, also referred to as a polymerase binding site. Such a process of extra steps to facilitate the amplification of double stranded DNA by transcription based amplification methods has been described in PCT patent application no. WO9602668 The extra steps described in this procedure do not only include extra handling steps, but also the use of additional ingredients, i.e. the E. coli RNA polymerase.

It has now been found that, in cases where the sample comprises double stranded DNA, a transcription based amplification process can be applied that is essentially isothermal and results in large amounts of RNA transcripts comprising the sequence of the DNA.

With the method of the present invention an isothermal transcription based amplification method is provided for the amplification of double stranded DNA. The method of the present invention for the amplification of double stranded DNA comprises the steps of contacting said double stranded DNA with at least one oligonucleotide comprising a sequence complementary to a part of the first of the two DNA strands comprised in the double stranded DNA, said oligonucleotide further comprising the sequence of a promoter recognized by a RNA polymerase a further oligonucleotide comprising a sequence complementary to a part of the second strand comprised in the double stranded DNA an enzyme having RNA dependent DNA polymerase activity an enzyme having DNA dependent DNA polymerase activity an enzyme having RNase H activity an enzyme having RNA polymerase activity and maintaining the thus created reaction mixture under the appropriate conditions for a sufficient amount of time for the amplification to take place.

The method according to the invention is particularly useful for amplifying small DNA molecules, e.g. plasmid DNA.

The method is particularly useful for the detection of small DNA molecules of pathogenic micro-organisms enabling diagnosis. In particular the circular HIV-1 DNA molecules that are formed during the replication of the HIV-1 virus can be detected by this method. Detection of such circular HIV-1 DNA molecules indicates active replication of the virus, which can be correlated with disease progression, i.e. development of AIDS. In another application the method can be used for detection of plasmid DNA molecules naturally present in Chlamydia species. The Chlamydia plasmids can encode certain virulence factors which means that detection of the plasmid not only shows the presence of the Chlamydia infection, but also shows the Chlamydia cells that cause the infection will carry certain virulence factors.

In yet other applications the method can be used for amplification of genomic sequences after (partial) degradation and isolation of the DNA. This has a wide range of applications, of which many can be associated with the detection and identification of mutations in the genomic DNA. These mutation can associated with the diagnosis of cancer, hereditary disease or predisposition for disease.

Surprisingly, transcription based amplification can start from double stranded DNA, without the need to treat the DNA with restriction enzymes or, what is more important, to separate the strands before hand by applying heat All reagents conventionally used with isothermal transcription based amplification reactions can simply be used on starting material containing double stranded DNA, as if it where single stranded RNA.

The enzymes used with the method according to the invention may be any enzymes that are known in the art as suitable enzymes for transcription based amplification methods and the reaction conditions are essentially the same as for prior art transcription based amplification methods, commonly used to amplify single stranded RNA. With the present invention it has now been found that essentially the same protocols can be used for isothermal transcription based amplification of double stranded DNA even though, based on the knowledge of the mechanisms according to which transcription based amplification reactions were suspected to operate, the skilled person would not have expected this method to be operable.

In a preferred embodiment the DNA is heated to 65 degrees Celsius in the presence of the amplification oligonucleotides, but not in the presence of the amplification enzymes. The enzymes are only added to the reaction after the reaction mixture is cooled to the incubation temperature for the amplification reaction, i.e. 41 degrees Celsius. In another embodiment of the method of the present invention the DNA can be heated to 100 degrees Celsius in the presence of the two amplification oligonucleotides. One skilled in the art would still not expect this method to work due to the fact that after oligonucleotide annealing and extension the newly made DNA strand has to be separated from the original DNA template strand before the second oligonucleotide can anneal and be extended. In this second preferred embodiment with only one heating step the enzymes are only added after the reaction mixture is cooled to the amplification incubation temperature, i.e. 41 degrees Celsius.

Preferably two oligonucleotides are used in the method according to the invention;

a first oligonucleotide (usually referred to a "promoter-primer") that is capable of hybridizing to a specific sequence in the first strand of the double stranded DNA, which oligonucleotide has the sequence of a promoter (for example the T7 promoter) attached to its 5' end and a second oligonucleotide ("primer") which comprises a sequence sufficiently complementary to a specific sequence on the second strand of the double stranded DNA. The sequences of the oligonucleotides should be chosen in such a way that they cannot hybridize to each other.

It is surprising that, by contacting the double stranded DNA with the two oligonucleotides and the appropriate enzymes, a transcription based amplification process can be performed wherein there is no need for several strand separation steps to separate the two strands making up the double stranded DNA. The method will result in multiple linear RNA copies comprising the target sequence that is part of the sequence of the double stranded DNA.

EXAMPLES

Preface

Figure 1:
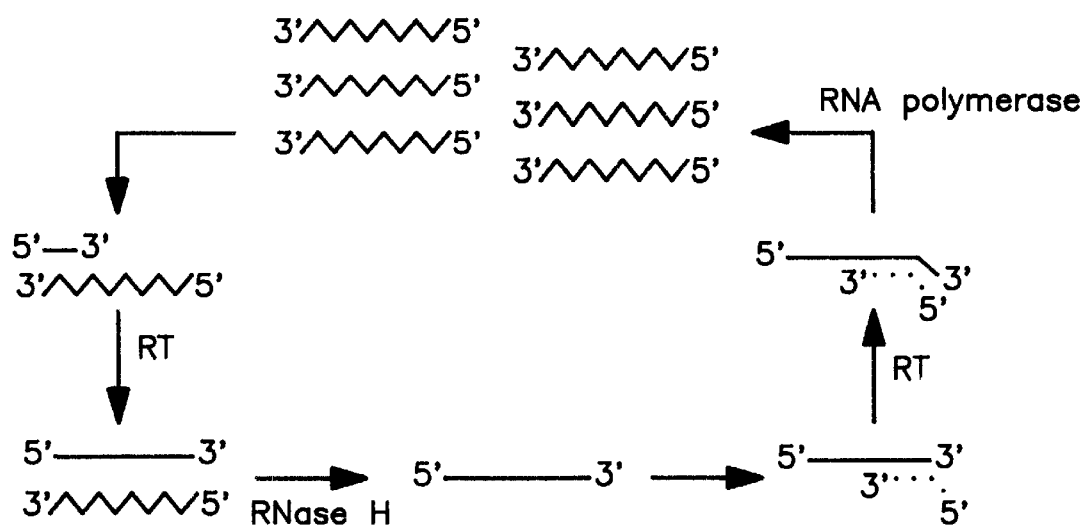
FIG. 1: reaction scheme for transcription based amplifications.

The following examples demonstrate the mechanism and utility of the present invention. They are not limiting and should not be considered as such. The enzymes used in the following examples are avian myeloblastosis virus (AMV) reverse transcriptase, T7 RNA polymerase and *E. coli* RNase H. Other enzymes with similar activities and enzymes from other sources may be used. Other RNA polymerases with different promoter specificity's may also be suitable for use.

The NASBA reaction conditions used in the following examples were 40 mM tris, pH 8.5, 42 mM KCl (or in later experiments 70 mM KCl), 12 mM $MgCl_2$, 5 mM DTT, 1 mM each dNTP, 2 mM rATP, 2 mM ICTP, 2 mM rUTP, 1.5 mM rGTP, 0.5 mM ITP, 0.2 $\mu$M each oligonucleotide, 375 mM sorbitol, 0.105 g/l BSA, 6.4 units AMV-RT, 32 units T7 RNA polymerase, 0.08 units *E. coli* RNase H and a specified amount of template in 20 $\mu$l volume. The oligonucleotide sequences used are exemplary and are not limiting as other sequences have been employed for these and other target sequences.

Example 1

To demonstrate the feasibility of DNA target amplification with NASBA without high temperature denaturation steps the two following oligonucleotides were used in combination with the above described NASBA reaction ingredients:

HIV-1 gag1 P1:

5'AAT TCTAATACG ACT CAC TATAGG GTG CTA TGT CAC TTC CCC TTG-GTTCTC TCA 3'

HIV-1 gag1 P2:

5'AGT GGG GGG ACA TCA AGC AGC CAT GCA AA 3'

The T7 promoter part of the P1 is given in italics. These primers target part of the gag region of the HIV-1 genome for amplification. As input for the amplification plasmid DNA pUCp24 encompassing the gag region of the HIV-1 genome was used in different input amounts. The protocol that was used consisted of mixing the target plasmid DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled HIV-1 gag probe 5' GAA TGG GAT AGA GTG CAT CCA GTG CAT G 3'. A positive result could be obtained with a sensitivity of $10^5$ molecules input of plasmid DNA in the amplification. The same results could be obtained with the same protocol without the 65° C. incubation.

Example 2

To demonstrate the feasibility of DNA target amplification with NASBA without high temperature denaturation steps the two following oligonucleotides were used in combination with the above described NASBA reaction ingredients:

HPV16 P1:

5'AAT TCTAATACG ACTCAC TATAGG GGA AAA ATA AAC TGT AAA TCA-TATTC 3'

HPV16 P2:

5'TTT GTT ACT GTG GTA GAT ACT AC 3'

The T7 promoter part of the P1 is given in italics. These primers target part of the HPV16 genome for amplification. As input for the amplification plasmid DNA pHPV16 containing a full length HPV16 genome was used in different input amounts. The protocol that was used consisted of mixing the target plasmid DNA with the ingredients described above in the preface except for the enzymes, heating to 65° C. , cooling to 41° C., addition of enzymes and incubation at 41° for 90 minutes. The amplified material was electrophoresed in an agarose gel, blotted onto a nylon filter and hybridized with the $^{32}$P-labeled HPV16 probe 5'AGT ACA AAT ATG TCA TTA TGT GC 3'. A positive result could be obtained with a sensitivity of 1 pg input of plasmid DNA in the amplification.

Example 3

To demonstrate the feasibility of DNA target amplification with NASBA without high temperature denaturation steps the two following oligonucleotides were used in combination with the above described NASBA reaction ingredients:

Chlamydia trachomatis natural plasmid P1:

5'AAT TCTAATACG ACT CAC TATAGG GCA AGA GTA CAT CGG TCA ACG-A 3'

Chlamydia trachomatis natural plasmid P2:

5'TCA CAG CGG TTG CTC GAA GCA 3'

The T7 promoter part of the P1 is given in italics. These primers target part of the Chlamydia trachomabs natural plasmid for amplification. As input for the amplification plasmid preparations from Chlamydia trachomatis were used in different input amounts relating to the amount of Chlamydia trachomatis Inclusion Forming Units (IFU's). The protocol that was used consisted of mixing the target plasmid DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled Chlamydia trachomatis natural plasmid probe 5'CGT GCG GGG TTA TCT TAA AAG GGA T 3'. A positive result could be obtained with an amount of plasmid DNA in the amplification corresponding to 0.01 IFU.

Example 4

To demonstrate the feasibility of DNA target amplification with NASBA without high temperature denaturation steps the two following oligonucleotides were used in combination with the above described NASBA reaction ingredients:

Tissue Factor P1:

5'AAT TCTMTACG ACT CAC TA TAGG GAG GGA ATC ACT GCT TGA 3'

Tissue Factor P2:

5'GAC CGT AGA AGA TGA ACG GA 3'

The T7 promoter part of the P1 is given in italics. These primers target part of the human Tissue Factor gene for amplification. As input for the amplification plasmid DNA pUC13-TF containing part of the Tissue Factor gene was used in different input amounts. The protocol that was used consisted of mixing the target plasmid DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled Tissue Factor probe 5'GTT CAG GAA AGA AAA CAG CA 3'. A positive result could be obtained with a sensitivity of 103 molecules of input of plasmid DNA in the amplification.

Example 5

To demonstrate the feasibility of DNA target amplification with NASBA without high temperature denaturation steps the two following oligonucleotides were used in combination with the above described NASBA reaction ingredients:

CD14 P1:

5'AAT TCTAATACG ACTCAC TATAGG GGG ATC TCC ACC TCT ACT GCA 3'

CD14 P2:

5'GAA GCT AAA GCA CTT CCA 3'

The T7 promoter part of the P1 is given in italics. These primers target part of the human CD14 gene for amplification. As input for the amplification plasmid DNA pπH3M containing part of the CD14 gene was used in different input amounts. The protocol that was used consisted of mixing the target plasmid DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled CD14 probe 5'CCA TGG AGC GCG CGT CCT 3'. A positive result could be obtained with a sensitivity of $10^3$ molecules of input of plasmid DNA in the amplification.

Example 6

To demonstrate the feasibility of DNA target amplification with NASBA without high temperature denaturation steps the two following oligonucleotides were used in combination with the above described NASBA reaction ingredients:

Actin P1:

5'AAT TCTAATACG ACTCAC TATAGG GGG A(AG)G GGC C(CG)G (AC)CT-CGTC(AG)T ACT 3'

Actin P2:

5'ATC AT(TC) GC(ATC) CC(GTC) CC(GAT) GAG CGC A 3'

The T7 promoter part of the P1 is given in italics. Nucleotides between brackets denote "degenerated" position were any of the nucleotides between the brackets can occur. These primers target part of the human Actin gene for amplification. As input for the amplification total human genomic DNA, (commercially obtained human placental DNA) treated with RNase A was used at 400 ng input amount. The protocol that was used consisted of mixing the target human placental genomic DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled Actin probe 5'CTG TCC ACC TTC CAG CAG ATG TGG A 3'. A positive result could be shown using the human genomic DNA as input for the amplification.

Example 7

To demonstrate the feasibility of DNA target amplification with NASBA without high temperature denaturation steps the two following oligonucleotides were used in combination with the above described NASBA reaction ingredients:

CMV-exon4 P1:

5'AAT TCTAATACT CAC TATAGG GAG ATC CTC AAT GCG GCG CTT CA 3'

CMV-exon4 P2:

5'GCT TGT ATG ATG ACC ATG TA 3'

The T7 promoter part of the P1 is given in italics. These primers target part of the CMV genoom for amplification. As input for the amplification total DNA of CMV infected HEL cells, treated with RNase A was used at an input amount equivalent to 0.1 cells. The protocol that was used consisted of mixing the DNA with the ingredients described above in the preface except for the enzymes, heating to 65° C., cooling to 41° C., addition of enzymes and incubation at 41° for 90 minutes. The amplified material was electrophoresed in an agarose gel, blotted onto a nylon filter and hybridized with the $^{32}$P-labeled CMV probe 5'CTG CTA TGT CTT AGA GGA GA 3'. A positive result could be shown using the DNA of 0.1 cell equivalent as input for the amplification.

What is claimed is:

1. A method for transcription based amplification of double stranded DNA, comprising the steps of:
   reacting the double stranded DNA with:
   a) at least one oligonucleotide comprising a sequence complementary to part of a first strand of the double stranded DNA, said oligonucleotide further comprising an RNA polymerase promoter sequence,
   b) another oligonucleotide comprising a sequence complementary to part of the second strand of the double stranded DNA,
   c) an enzyme having RNA dependent DNA polymerase activity,
   d) an enzyme having DNA dependent DNA polymerase activity,
   e) an enzyme having Rnase H activity, and
   f) an enzyme having RNA polymerase activity, and
   maintaining the reaction mixture under appropriate isothermal conditions, and in the absence of heat treatment after addition of the above enzymes, for a sufficient amount of time to amplify the double stranded DNA.

2. The method of claim 1, wherein the double stranded DNA is heated once in the presence of the oligonucleotides, but before addition of the amplification enzymes.

3. The method of claim 2, wherein the double stranded DNA is heated to 65° C.

4. The method of claim 2, wherein the mixture is heated to 100° C.

5. The method of claim 1, wherein the double stranded DNA is a plasmid DNA or genomic DNA.

6. The method of claim 5, wherein the genomic DNA has been partially degraded.

7. The method of claim 1, further comprising reverse transcriptase.

8. The method of claim 7, wherein the reverse transcriptase is AMV reverse transcriptase.

9. The method of claim 1, wherein the RNA polymerase promoter sequence is the T7 promoter sequence and the enzyme having RNA polymerase activity is T7 RNA polymerase.

10. The method of claim 1, further comprising Rnase H.

* * * * *